United States Patent [19]

Hocker

[11] Patent Number: 5,430,384
[45] Date of Patent: Jul. 4, 1995

[54] TEMPERATURE COMPENSATED SOIL MOISTURE SENSOR

[75] Inventor: Lon Hocker, Falmouth, Mass.

[73] Assignee: Onset Computer Corp., Pocasset, Mass.

[21] Appl. No.: 284,881

[22] Filed: Jul. 22, 1994

[51] Int. Cl.[6] ...................... G01R 27/26; F16K 31/18
[52] U.S. Cl. ..................... 324/694; 137/78.3
[58] Field of Search ............... 324/724, 694, 696, 721, 324/441; 73/336.03, 336.04, 336.05; 137/78.3

[56] References Cited

U.S. PATENT DOCUMENTS

| 3,553,481 | 7/1968 | Hasenbeck | 324/694 |
| 3,882,383 | 5/1975 | Matlin | 324/65 R |
| 4,132,944 | 1/1979 | Bentz | 324/441 |
| 4,137,937 | 2/1979 | Hasenbeck | 137/78.3 |
| 4,197,866 | 4/1980 | Neal | 137/78.3 |
| 4,227,151 | 10/1980 | Ellis et al. | 324/441 |
| 4,823,087 | 4/1989 | Sugimori | 324/721 |
| 4,993,640 | 2/1991 | Baugh | 137/78.3 |
| 5,040,417 | 8/1991 | Rowlette | 324/694 |
| 5,103,179 | 4/1992 | Thomas et al. | 324/441 |
| 5,148,826 | 9/1992 | Bakhshaer | 137/78.3 |
| 5,179,347 | 1/1993 | Hawkins | 324/696 |
| 5,207,380 | 5/1993 | Harryman | 137/783 |

FOREIGN PATENT DOCUMENTS

| 0083240 | 5/1983 | Japan | 324/721 |
| 0640196 | 12/1978 | U.S.S.R. | 324/441 |
| 0702287 | 12/1979 | U.S.S.R. | 324/696 |

OTHER PUBLICATIONS

Pogue, William R., Watermark Soil Moisture Sensor—an Update, Dec. 1990, pp. 2-4.

Primary Examiner—Maura K. Regan
Attorney, Agent, or Firm—Holmes W. Anderson

[57] ABSTRACT

A resistive soil moisture sensor which is implanted in the soil includes a temperature sensitive component, located at the same soil depth as the sensor. The thermistor is part of a thermistor network which includes other components which are located above ground. The resultant sensor automatically compensates for temperature variations, and is well suited for use with data loggers and automatic control systems.

4 Claims, 6 Drawing Sheets

TEMPERATURE COMPENSATED SOIL MOISTURE SENSOR

TECHNICAL FIELD

This invention relates to soil moisture sensors, and more particularly to a temperature compensated soil moisture sensor which is useful in conjunction with data loggers and other electronic devices.

BACKGROUND OF THE INVENTION

Estimating soil moisture content by measuring the resistance between electrodes which are placed in the soil is well known. Moisture in the soil provides a conductive path between the electrodes. As the soil becomes more moist, the resistance between the electrodes decreases. In dry soil the resistance between the electrodes is high. A response curve providing soil moisture as a function of resistance for a particular soil type can be determined through testing. Thus, by burying electrodes in the soil and monitoring the resistance between the electrodes, soil moisture content can be estimated. In practice, however, a number of other factors effect the resistance between the electrodes.

In their most basic form, resistive soil moisture sensors consist of two electrodes which are placed in direct contact with the soil. U.S. Pat. No. 3,882,383 entitled SOIL MOISTURE SENSING SYSTEM issued to Matlin is exemplary. Unfortunately, sensors with electrodes in direct contact with the soil are adversely effected by variations in both soil particle size and soil moisture conductivity. Since soil particle size and soil moisture conductivity vary greatly from place to place, such sensors are difficult to work with and often provide relatively inaccurate data.

More advanced soil moisture sensors include a housing filled with a filter medium which shields the electrodes from direct contact with the soil. U.S. Pat. No. 5,179,347 entitled ELECTRICAL SENSOR FOR SENSING MOISTURE IN SOILS issued to Hawkins is exemplary. The filter medium in which the electrodes are embedded contains particles of uniform size. The use of the filter medium alleviates the problem associated with variations in soil particle size. The sensor may also include a gypsum buffer tablet to address the problem associated with variation in soil moisture conductivity. However, there is another factor which effects the accuracy of the sensor. This and other known types of soil moisture sensors are substantially temperature dependent. At any given soil moisture content, as temperature decreases, resistance between the electrodes increases. Consequently, if the soil temperature varies while logging data, the resulting data is inaccurate.

Overcoming the temperature dependence problem would allow development of a number of useful applications of soil moisture sensors. One particular area where soil moisture sensors hold great promise is agriculture. Soil moisture sensors could be used in conjunction with automatic irrigation systems to minimize water waste and runoff. Further, by using such sensors in conjunction with data loggers, agronomists could profile changes in soil moisture over time. Such loggers could be placed in remote sites where frequent, long term measurement would otherwise be impossible.

It is known to make a manual temperature compensation based on surface temperature. Typically, a person must visit the measurement site at regular intervals and adjust the logging or measuring device according to the then current surface temperature. This method has at least two major drawbacks. First, surface temperature is often very different from soil temperature. Consequently, error is introduced into the temperature compensation calculation as a result of the difference between surface temperature and soil temperature at the depth of the sensor. This problem becomes more pronounced as the sensor is placed deeper in the soil. Second, data loggers take measurements at regular intervals, there very purpose being to obviate the need for a person to be at the logging site to take measurements. In order to use surface compensation, a person must visit the site frequently. Such frequent visits substantially raise the cost of running the data logging device and still produce relatively inaccurate data. In practical terms, the need for frequent visits nullifies the advantages of using a data logger.

Of course, there are many other uses for soil moisture sensors apart from their use in conjunction with data loggers and automatic irrigation systems. It is therefore desirable to have a soil moisture sensor which is compensated for changes in temperature.

SUMMARY OF THE INVENTION

An object of the present invention is to provide an improved soil moisture sensor.

Another object of the present invention is to provide a temperature compensated soil moisture sensor.

Yet another object of the present invention is to provide a temperature compensated soil moisture sensor which is suitable for use with an electronic data logger.

Even yet another object of the present invention is to provide a temperature compensated soil moisture logger.

Even yet still another object of the present invention is to provide a temperature compensated soil moisture sensor which is inexpensive to manufacture.

According to the present invention, a temperature compensated soil moisture sensor for measuring soil moisture content at a given soil depth comprises: a housing; an electrode matrix disposed within said housing; a first electrode connected to said electrode matrix; a second electrode connected to said electrode matrix; and a temperature sensitive component, said temperature sensitive component connected to said first electrode, and located at substantially the same soil depth as said electrode matrix when said soil moisture sensor is in use.

A primary feature of the present invention is the temperature sensitive component which is located at substantially the same soil depth as the sensor. Previously, temperature compensation has been based on surface temperature. Because surface temperature may differ substantially from subsurface temperature, this prior art method is particularly inaccurate. By placing the temperature sensitive component at the point where soil moisture is being measured, the present invention provides much more accurate temperature compensation than any method known under the prior art.

An advantage of the present invention is fully automatic temperature compensation. Prior art temperature compensation schemes have been manual. As such, they must be attended to frequently. The present invention allows long term deployment of, for example, soil moisture data loggers, in sites where frequent manual compensation is too costly or impractical.

The present invention allows heretofore impossible scientific research to be performed. Soil moisture measurement is important to environmental research and natural resource management. Often, it is desirable to have soil moisture measurements taken in harsh environments where temperature may vary widely, and where frequent manual adjustment is impossible. By automatically compensating for temperature variations, the present invention makes such research possible.

The present invention provides more reliable and efficient automatic irrigation systems. Most automatic irrigation systems are triggered to begin and cease irrigation by a timer. Timer based systems are particularly inefficient since they allow water to flow for a given time regardless of the soil moisture content. Thus, even after many days of rainfall when the soil is saturated with water, such a system continues to water a field in a preprogrammed manner. Uncompensated soil moisture sensors might provide slightly more efficient irrigation systems. However, because they are temperature dependent, such systems must be manually adjusted on a regular basis. The temperature compensated soil moisture sensor of the present invention decreases the cost of running automatic irrigation systems by eliminating the need for manual temperature compensation. Temperature compensated systems also conserve water by halting irrigation when an appropriate soil moisture level is reached.

Other objects, features and advantages of the invention will become apparent in light of the following description thereof.

BEST MODE FOR CARRYING OUT THE INVENTION

Figure 1:
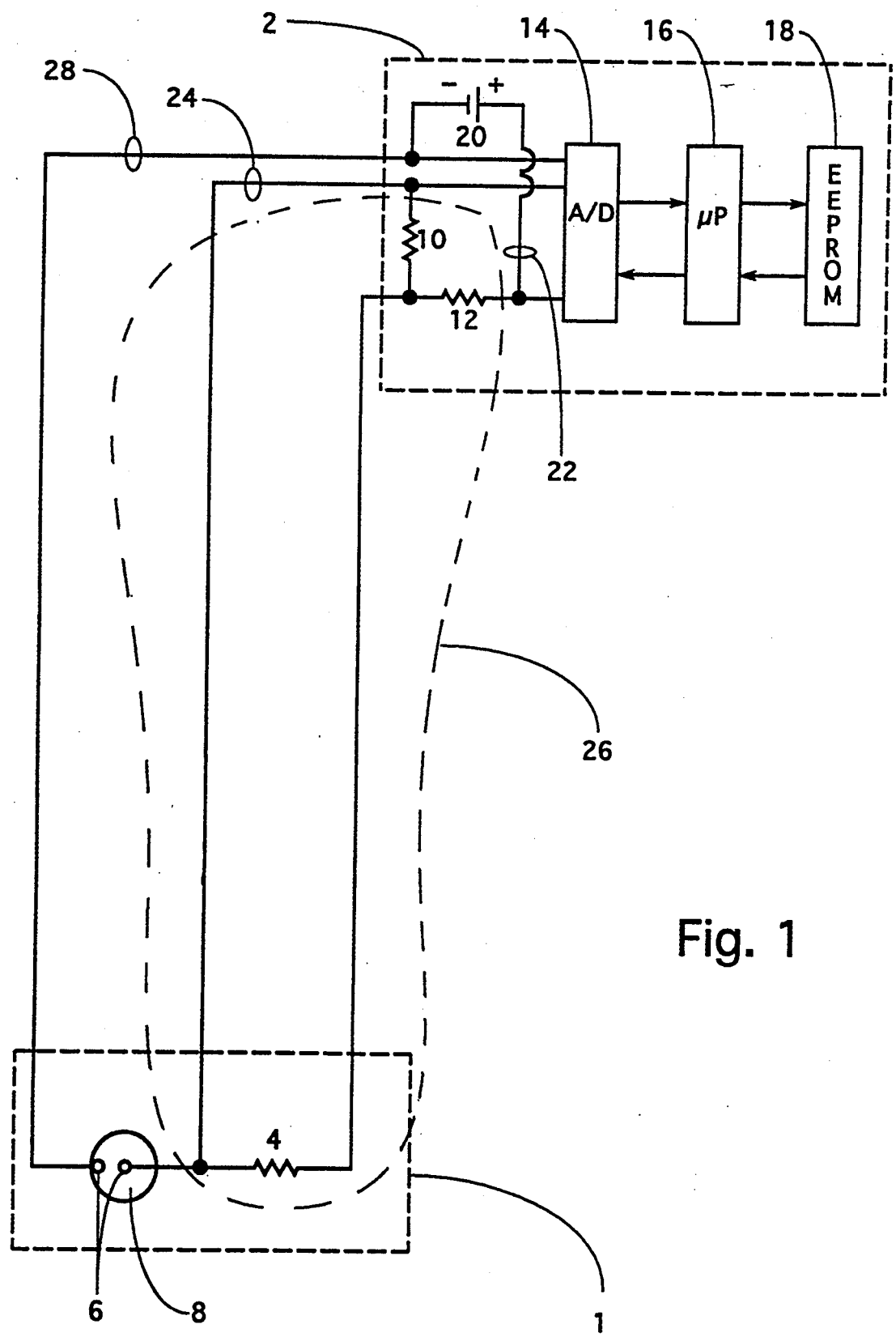
FIG. 1 is a schematic/block diagram of a temperature compensated soil moisture sensor in conjunction with a data logger.

FIG. 1 is a schematic/block diagram of a temperature compensated soil moisture sensor i configured for use with and partially integrated into a data logger 2. The sensor includes a thermistor 4, and two electrodes 6 in an electrode matrix 8. The electrodes and electrode matrix may be the type described in U.S. Pat. No. 5,179,347 entitled ELECTRICAL SENSOR FOR SENSING MOISTURE IN SOILS, issued to Hawkins Jan. 12, 1993, which is incorporated herein by reference. The data logger includes a first resistor 10, a second resistor 12, an analog to digital ("A/D") converter 14, a microprocessor 16, a memory 18, and a battery 20.

The logger 2 and sensor 1 function to record measurements of soil moisture at a given depth below the surface of the/soil (not illustrated). The microprocessor 16 is connected to the memory 18, and functions to direct measurement taking. The A/D converter 14 is also connected to the microprocessor, and functions to translate an analog voltage (not illustrated) across the electrode matrix 8 to digital. The battery 20, or other voltage source, is connected to a voltage supply line 22. The second resistor 12 is connected to the voltage supply line. An output voltage line 24 is connected to the A/D converter 14. The first resistor 10 is connected between the output voltage line 24 and the second resistor 12. The second resistor is connected between the first resistor 10 and the battery 20. The thermistor 4 is connected in parallel with the first resistor 10. Together, the thermistor, first resistor, and second resistor form a thermistor network 26. The thermistor network has a temperature response characteristic (not specifically illustrated) which is substantially the same as that of the electrode matrix 8. The electrode matrix and the battery are also connected through a return line 28.

Figure 4:
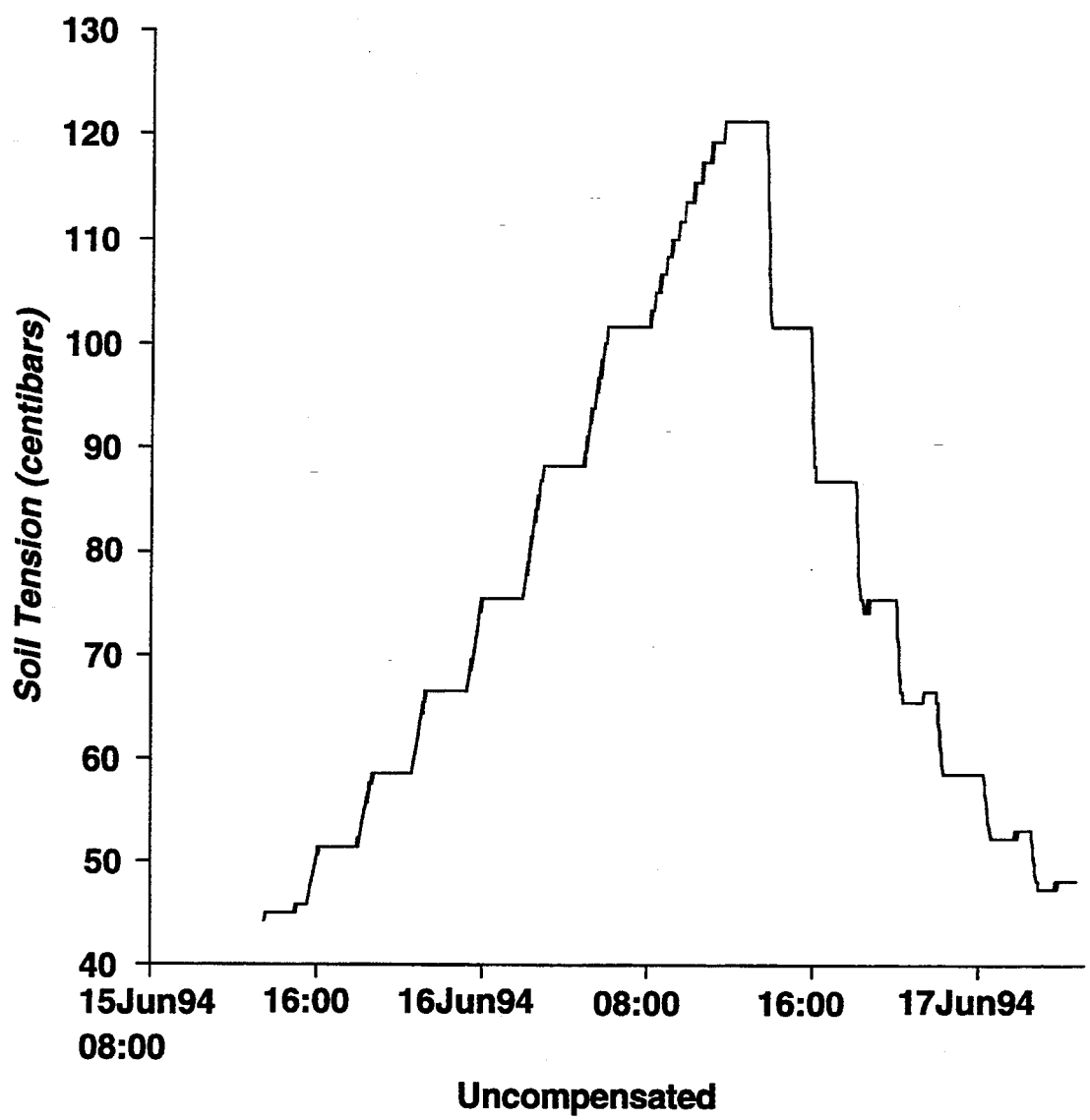
FIG. 4 is a Graph illustrating the response of an uncompensated soil moisture sensor to changes in temperature from 0° to 35° C.

The electrode matrix 8 is typical of those found in the prior art. The matrix is operative to change its moisture content, and thus its resistance, as a function of soil moisture content. As moisture (not illustrated) enters the electrode matrix, resistance between the electrodes 6 decreases. The decrease in resistance is due to the conductivity of the moisture. The resistance between the electrodes increases as moisture exits the electrode matrix. The amount of moisture present in the soil is estimated based on the resistance between the electrodes. As in the prior art, the resistance of the electrode matrix 8 alone is temperature dependent. At a given moisture level, as temperature increases resistance decreases. FIG. 4 is illustrative of the effects of temperature on a typical electrode matrix.

Turning back to FIG. 1, the thermistor network 26 provides temperature compensation for the electrode matrix 8. The thermistor 4, first resistor 10, and second resistor 12 together have a temperature characteristic (not illustrated) which is substantially the same as that of the electrode matrix 8. The thermistor is placed at substantially the same soil depth as the electrode matrix in order to provide accurate temperature compensation, i.e., within several inches of the matrix. Suitable thermistor 4 and resistor 10, 12 values can be determined for any particular electrode matrix ratiometrically. The resistance value of the second resistor is about ten times the resistance value of the first resistor. The resistance value of the second resistor is also about ten times the resistance value of the thermistor at 25° C. For an uncompensated matrix such as that found in the Watermark #200-10 manufactured by the Irrometer Company, a 5100Ω first resistor, 62KΩ second resistor and a 5K@25° C. thermistor such as the 5K3A1 manufactured by BetaTHERM Corporation provide adequate temperature compensation. Other uncompensated matrices have a temperature dependence which is proportional to that of the Watermark #200-10. For such matrices, resistance values of the thermistor 4 and resistors 10, 12 should be adjusted accordingly while maintaining about a 10:1 ratio, or preferably about 12:1.

The data logger 2 is operative to automatically take and store soil moisture data. The microprocessor 16 directs measurements to be taken by the A/D converter 14 at regular intervals. The battery 20 is used to power the A/D converter 14, microprocessor 16 and memory 18, and to provide a potential across the electrode matrix 8. In order to minimize battery drain through the sensor 1, and also to prevent the electrodes 6 from becoming polarized, the voltage supply line 22 is switched to be activated just prior to taking a measurement and inactivated after the measurement is taken. Measurements are taken approximately 2 ms into a voltage pulse which is applied to the voltage supply line 22. The polarization problem may also be addressed by using an AC voltage rather than a DC voltage on the voltage supply line. The voltage across the electrode matrix 8 is converted to a digital value in the A/D converter 14. The digital value is fed to the microprocessor 16 and then stored in the memory 18.

Figure 2:
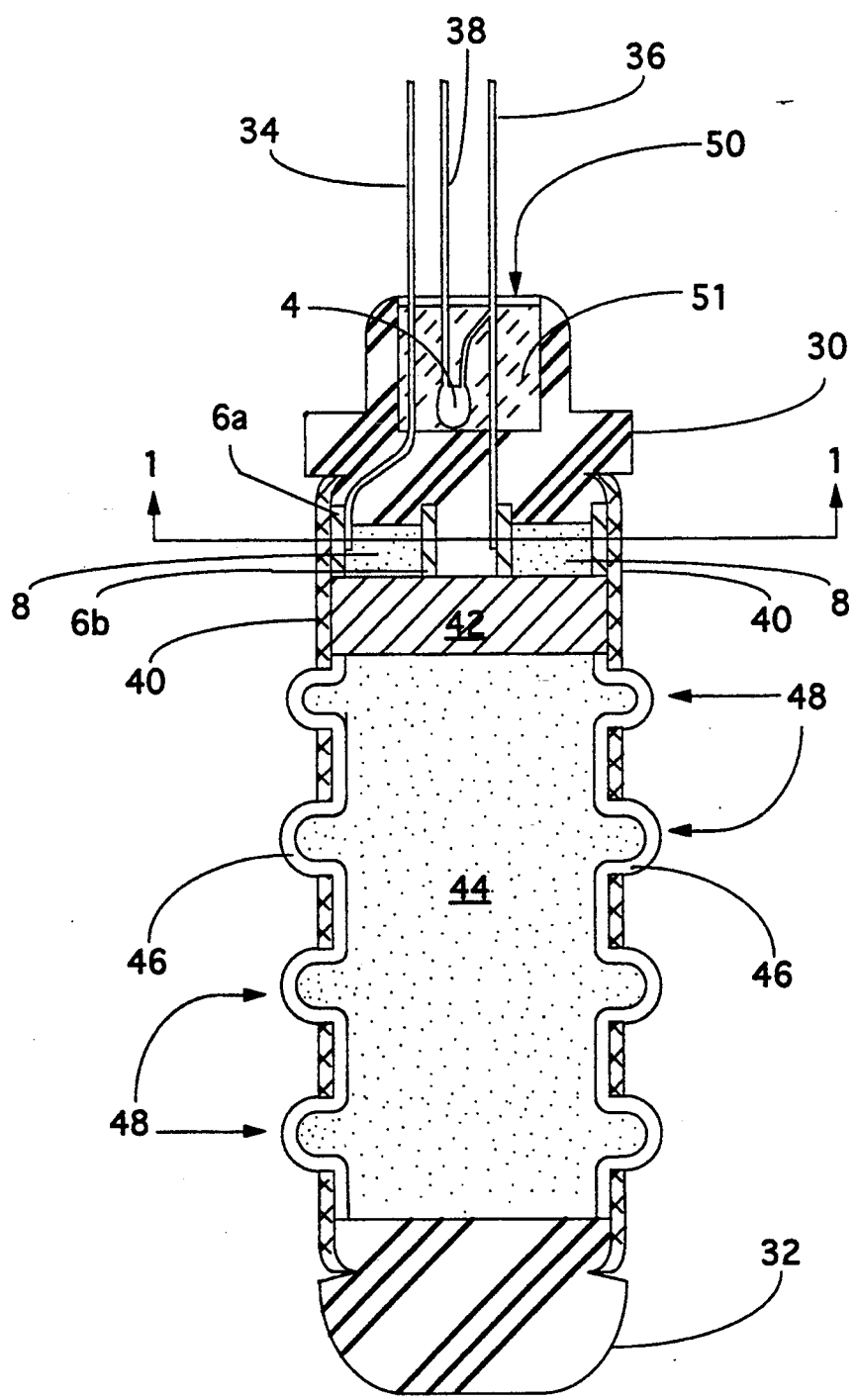
FIG. 2 is a cutaway view of the soil moisture sensor of FIG. 1.

FIG. 2 is a cutaway view of the soil moisture sensor 1 of FIG. 1. The sensor includes a top end cap 30, a bottom end cap 32, a first lead 34, a second lead 36, a first electrode 6a, a second electrode 6b, a third lead 38, the thermistor 4, a cylindrical metal housing 40, the electrode matrix 8, a buffer matrix 42, a transfer matrix 44, and a liner 46.

The transfer matrix 44, buffer matrix 42 and electrode matrix 8 are enclosed in the cylindrical housing 40. The bottom end cap 32 is secured in place by pinching the metal housing 40 in upon the plastic end caps 30, 32. The housing is constructed of conductive metal which is perforated adjacent to the transfer matrix 44 to allow moisture to freely enter and exit the sensor. The transfer matrix and electrode matrix are moisture permeable and comprised of silica sand.

The transfer matrix 44 acts as a filter. If particulate matter is allowed to flow into the electrode matrix 8, the output of the sensor may be adversely affected. The silica sand transfer matrix is therefore located between surrounding soil and the electrode matrix to prevent particulate matter from entering the electrode matrix. The liner 46 is placed between the transfer matrix and perforations 48 in the housing 40 to prevent the silica sand from exiting the sensor through the perforations.

The buffer matrix 42 functions to compensate for variation in soil moisture conductivity. The buffer matrix is located between the transfer matrix 44 and electrode matrix 8, and may be constructed of compacted gypsum. The electrode matrix is compacted between the electrodes 6a, 6b. The first and second leads 34, 36 are connected to the first and second electrodes 6a, 6b, respectively, and pass through the plastic top 30. The top includes a cavity 50 in which the thermistor 4 is placed. The thermistor is potted in the cavity with urethane 51.

Figure 3:
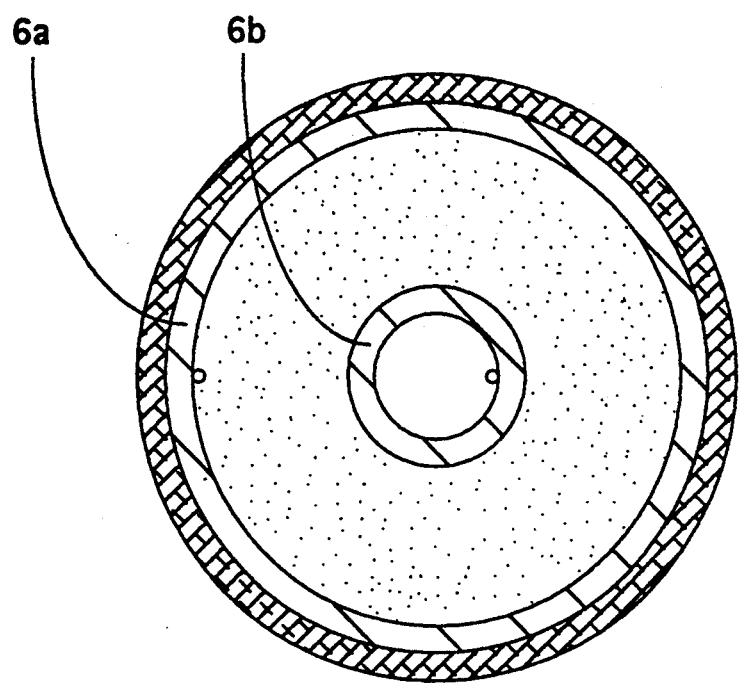
FIG. 3 is an enlarged cross sectional view of the soil moisture sensor of FIG. 2 taken along line 1—1.

FIG. 3 is an expanded cross sectional view of the soil moisture sensor of FIG. 2 taken along line 1—1. The cross section illustrates the shape of the electrodes 6a, 6b and the electrode matrix 8.

Figure 5:
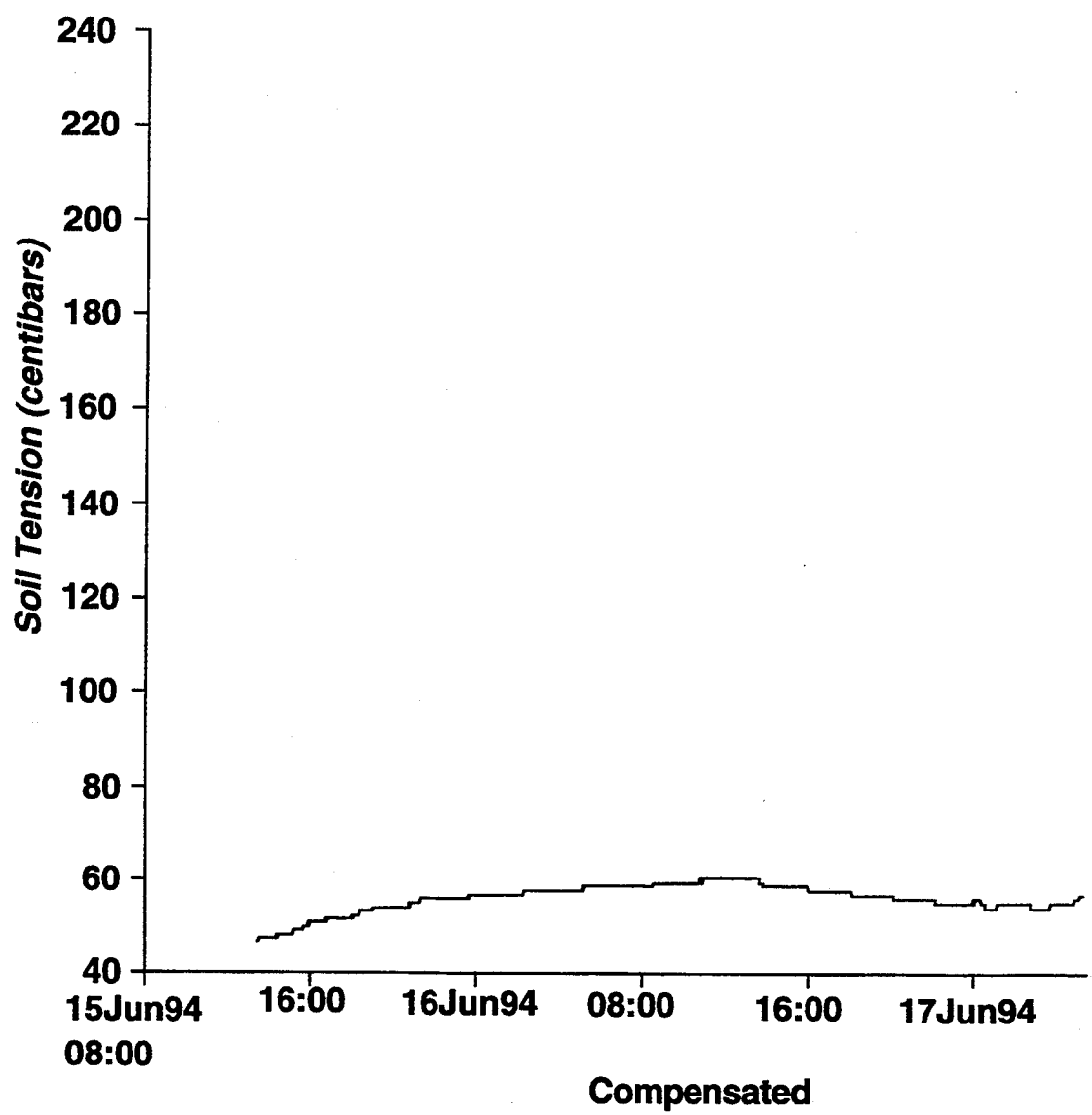
FIG. 5 is a Graph illustrating the response of a temperature compensated soil moisture sensor to the same changes in temperature as the uncompensated sensor of FIG. 4.
Figure 6:
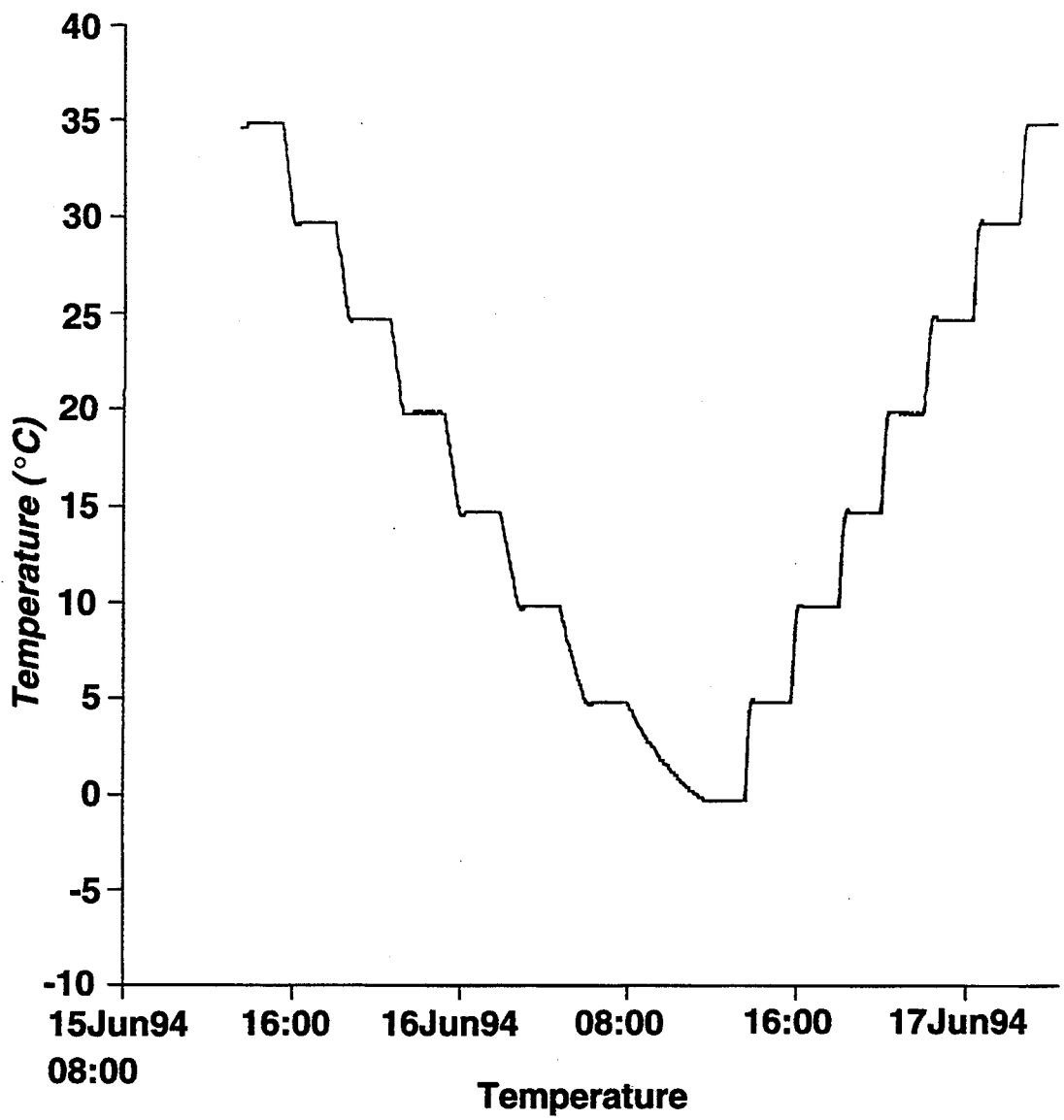
FIG. 6 is a Graph illustrating the temperature changes associated FIGS. 4 and 5.

FIGS. 4 and 5 are Graphs which illustrate, respectively, the response of an uncompensated and a compensated soil moisture sensor to changes in temperature between 0° and 35° C. FIG. 6 illustrates the temperatures at which the responses of FIGS. 4 and 5 were produced. Apart from temperature compensating circuitry, the sensors of FIGS. 4 and 5 are identical. Both sensors were held at a substantially constant moisture level of about 45 centibars in a plastic bag in a temperature bath. The temperature was then dropped from 35° to 0° C. in steps of 5° C., and then raised back up to 35° C. in the same steps. As is evident from FIG. 4, the output of the uncompensated sensor varied by as much as a factor of three in response to the temperature changes. Such a large variation would render data gathered for most any purpose totally useless, and would cause disastrous results if used to prompt an automatic irrigation system. In contrast, the maximum variation of the temperature compensated sensor constructed according to the present invention is a factor of about 1.2, which is acceptable over this temperature range for most applications.

A variety of modifications and variations of the present invention are possible in light of the above teachings. It is therefore to be understood that, within the scope of the appended claims, the present invention may be practiced otherwise than specifically described herein above.

What is claimed is:

1. A temperature compensated soil moisture sensor for measuring soil moisture content in soil surrounding said sensor at a given depth in the soil, which comprises:
   a moisture permeable housing;
   a moisture permeable electrode matrix disposed within said housing such that soil moisture passes from the soil, through said housing, and into said electrode matrix;
   a first electrode connected to said electrode matrix;
   a second electrode connected to said electrode matrix such that a resistance measured between said first and second electrodes is indicative of soil moisture content in the soil surrounding said sensor; and
   means for compensating for changes in the resistance between said first and second electrodes caused by changes in soil temperature, said temperature compensation means consisting of a thermistor and a plurality of resistors connected to said first electrode such that said thermistor is located at substantially the same depth in the soil as said electrode matrix when said soil moisture sensor is in use, said compensating means not including an arithmetic divider;
   whereby an existing soil moisture sensor can be easily retrofitted with temperature compensation by potting said thermistor in a top end cap of the existing sensor.

2. The temperature compensated soil moisture sensor of claim 1, wherein said temperature compensating means consists of a first resistor and a second resistor and said thermistor, said thermistor and said first resistor arranged in parallel and connected to said first electrode, said second resistor connected between said parallel thermistor and first resistor and a voltage supply line.

3. The temperature compensated soil moisture sensor of claim 2, wherein said first and second resistors and said thermistor have particular resistance values, said resistance value of said second resistor being about ten times said resistance value of said first resistor, and further wherein said resistance value of said second resistor is about ten times said resistance value of said thermistor at 25° C.

4. The temperature compensated soil moisture sensor of claim 2, wherein the resistance value of said first resistor is 5100Ω, the resistance value of said second resistor is 62kΩ, and the resistance value of said thermistor is 5kΩ at 25° C.

\* \* \* \* \*